(12) United States Patent
Rago et al.

(10) Patent No.: US 10,124,503 B2
(45) Date of Patent: Nov. 13, 2018

(54) BENCH TOP BOARD SCORING DEVICE

(71) Applicant: UNITED STATES GYPSUM COMPANY, Chicago, IL (US)

(72) Inventors: William J. Rago, Gurnee, IL (US); Charles W. Cochran, Elkhorn, WI (US)

(73) Assignee: UNITED STATES GYPSUM COMPANY, Chicago, IL (US)

( * ) Notice: Subject to any disclaimer, the term of this patent is extended or adjusted under 35 U.S.C. 154(b) by 0 days.

(21) Appl. No.: 15/419,476

(22) Filed: Jan. 30, 2017

(65) Prior Publication Data
US 2018/0215059 A1    Aug. 2, 2018

(51) Int. Cl.
*B27B 1/00* (2006.01)
*B27B 17/00* (2006.01)
*B27B 15/00* (2006.01)
*B26D 3/08* (2006.01)
(Continued)

(52) U.S. Cl.
CPC ........... *B26D 3/085* (2013.01); *B26D 7/2614* (2013.01); *G01N 3/08* (2013.01); *G01N 2203/0003* (2013.01); *G01N 2203/0012* (2013.01); *G01N 2203/0041* (2013.01); *G01N 2203/0096* (2013.01)

(58) Field of Classification Search
CPC ..... B27B 1/00; B27B 17/0058; B27B 17/005; Y10T 83/7101; Y10T 83/7264; Y10T 83/8876; Y10T 83/4705; Y10T 83/476; Y10T 83/8801; Y10T 83/4667; Y10T 83/4696; Y10T 83/4763; Y10T 83/4679; Y10T 83/4676; Y10T 83/8822; B26D 1/04; B26F 1/02

USPC ...... 83/879, 820, 646, 644, 647.5, 290, 293, 83/294, 300, 303, 599, 620, 319, 320, 83/886, 614, 796, 382, 574, 799; 144/378

See application file for complete search history.

(56) References Cited

U.S. PATENT DOCUMENTS

| 1,670,946 A | * | 5/1928 | Wolf | ...................... B27G 19/02 83/471.2 |
| 2,225,630 A | * | 12/1940 | Gilbert | ...................... B31F 1/08 493/372 |

(Continued)

OTHER PUBLICATIONS

International Search Report from corresponding International Patent Application No. PCT/US2018/015373, dated May 24, 2018.

*Primary Examiner* — Ghassem Alie
(74) *Attorney, Agent, or Firm* — Greer, Burns & Crain, Ltd.; Pradip Sahu; Philip T. Petti

(57) ABSTRACT

A bench top board scoring device is provided, having a frame having a first end and an opposite second end, a work area defined between the first and second ends, each end having at least one leg configured for contacting a substrate. A track is connected to the frame and extends between the first end and the second end, a carriage is slidably mounted to the track for travel between the first end and the second end, and an arm has an upper surface, a pivot end pivotally connected to the carriage, and an opposite knife mount end. A knife blade is mounted to the knife mount end. Additionally, the present device is constructed and arranged so that as the carriage is moved from the first end to the second end, wallboard samples placed in the work area and contacted by the knife blade receive a constant scoring force.

17 Claims, 6 Drawing Sheets

(51) Int. Cl.
*G01N 3/08* (2006.01)
*B26D 7/26* (2006.01)

(56) References Cited

U.S. PATENT DOCUMENTS

| | | | | |
|---|---|---|---|---|
| 2,401,500 A * | 6/1946 | Ockfen | ............... | B27L 1/10 |
| | | | | 144/208.6 |
| 2,409,203 A * | 10/1946 | Gale | ............... | B26D 1/045 |
| | | | | 411/937.2 |
| 3,155,909 A * | 11/1964 | Shepherd | ............... | H04B 1/40 |
| | | | | 455/524 |
| 3,618,369 A | 11/1971 | Hamilton et al. | | |
| 3,656,385 A * | 4/1972 | Kimbrell | ............... | B26D 1/04 |
| | | | | 83/290 |
| 4,033,572 A * | 7/1977 | Cailloux | ............... | B21D 5/002 |
| | | | | 269/320 |
| 4,350,067 A * | 9/1982 | Picard | ............... | B27B 17/0058 |
| | | | | 269/296 |
| 4,606,252 A * | 8/1986 | Lahti | ............... | B27B 17/0058 |
| | | | | 83/574 |
| 4,611,521 A * | 9/1986 | McCardle | ............... | B27B 17/0058 |
| | | | | 30/382 |
| 4,635,515 A | 1/1987 | Altman | | |
| 5,950,517 A * | 9/1999 | Yoder | ............... | B27B 29/085 |
| | | | | 144/250.24 |
| 6,467,174 B1 | 10/2002 | Kotori | | |
| 7,475,599 B2 | 1/2009 | Frank et al. | | |
| 8,122,805 B2 * | 2/2012 | Liu | ............... | B26D 5/10 |
| | | | | 30/218 |
| 2011/0179929 A1 * | 7/2011 | Angel | ............... | B26D 1/04 |
| | | | | 83/614 |
| 2012/0037276 A1 * | 2/2012 | Granberg | ............... | B27B 1/00 |
| | | | | 144/378 |
| 2015/0217469 A1 | 8/2015 | Vogeler et al. | | |
| 2015/0306779 A1 * | 10/2015 | Napolitano | ............... | B26D 3/085 |
| | | | | 83/880 |

* cited by examiner

BENCH TOP BOARD SCORING DEVICE

BACKGROUND

The present invention relates to testing devices for construction materials, and more specifically to a device for consistently testing gypsum wallboard construction panels for their performance when scored and fractured along the score line.

It is customary among construction workers that when installing wallboard panels, the panels can be easily trimmed to size by scoring the paper facing with a utility knife, then impacting the panel by hand pressure along the score line to cause the panel to fracture. Such a procedure is sometime referred to as "scoring and popping" or "scoring and breaking" the panel. If performed properly, the panel will neatly and completely fracture along the score line. An improperly scored and popped panel requires additional labor to create a true, flat popped edge. In addition, the conventional rasping procedure used to correct the popped edge creates unwanted dust in the workplace. Also, it has been found that different types of wallboard panels, and panels manufactured by different source companies, often have different scoring and popping characteristics. It is desirable for practitioners, as well as wallboard manufacturers to be able to evaluate competitive construction panels for their scoring and popping performance.

Thus, there is a need for a device that is constructed and arranged to compare manufactured wallboard products across brand lines as to their performance relating to scoring and breaking.

SUMMARY

The above-listed need is met or exceeded by the present bench top board scoring device, which features the ability to apply a constant weight and angle of a cutting knife to determine how smooth the "break" of the core will be by applying a constant angle and pressure while scoring. In the preferred embodiment, a rigid frame, preferably made of aluminum strut channel, defines a working area of approximately 5 feet in length, which has the capacity for scoring several samples in one pass. A moving carriage is secured to the frame for travel from one end to the other. To reduce friction, the carriage is equipped with relatively low friction linear bearings. An arm is pivotably joined to the carriage and is configured for holding a cutting knife, constructed for receiving a conventional shop knife blade as used in the field for board scoring.

A zero lash bearing is used to join the arm to the frame to prevent lateral arm movement during testing. Also, the linear bearings on the carriage force the blade to travel in a perfectly straight line as the carriage is moved relative to the frame, thus reducing the impact of human error in any test procedure. A constant weight is applied to the blade via the use of barbell discs mounted on a generally vertically projecting weight post connected to an upper surface of the arm. The present testing device is constructed and arranged so that as the carriage is moved from the first end to the second end of the frame, wallboard samples placed in the work area and contacted by the knife blade receive a constant scoring force.

After scoring, the boards passed through the present device are tested on a constant motion machine or other testing machine which tests the strengths properties of gypsum wallboard panels by applying a constant speed or load to panel samples until they fail, at which time a load reading is recorded. Next, technicians examine the cut gypsum edge for flatness. In this analysis, it is determined whether the breaking force is consistent compared to other samples from a similar source, such as a particular production plant or a particular brand.

Another feature of the present device is that since flatter gypsum edges are produced after "scoring and popping," less dust is generated, as compared to the conventional rasping process used to prepare the board edge for butt joints.

More specifically, the present invention provides a bench top board scoring device, including a frame having a first end and an opposite second end, a work area defined between the first and second ends, each end having at least one leg configured for contacting a substrate. A track is connected to the frame and extends between the first end and the second end. A carriage is slidably mounted to the track for travel between the first end and the second end, and an arm has an upper surface, a pivot end pivotally connected to the carriage, and an opposite knife mount end. A knife blade is mounted to the knife mount end. The present device is constructed and arranged so that as the carriage is moved from the first end to the second end, wallboard samples placed in the work area and contacted by the knife blade receive a constant scoring force.

In another embodiment, a bench top board scoring device is provided, including a frame having a first end and an opposite second end, a work area defined between the first and second ends, each end having at least one leg configured for contacting a substrate. A track is connected to the frame and extends between the first end and the second end. A carriage is slidably mounted to the track for travel between the first end and the second end, and an arm has an upper surface, a pivot end pivotally connected to the carriage, and an opposite knife mount end. A knife blade is mounted to the knife mount end. A weight post is associated with, and projects from the arm, and is constructed and arranged for receiving weights for exerting a force on the arm. A power transmission element is connected to the carriage for achieving user-generated movement of the carriage along the track.

DETAILED DESCRIPTION

Figure 1:
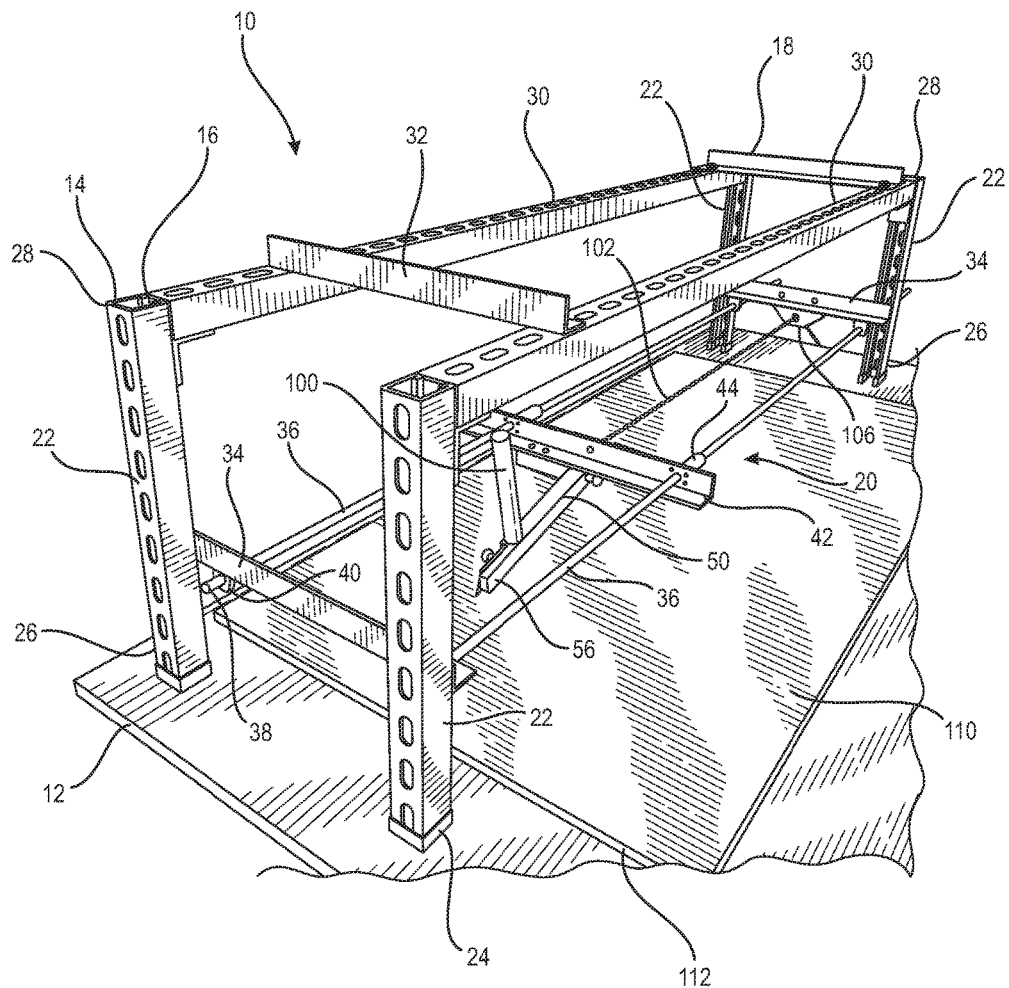
FIG. 1 is a top front perspective view of the present board scoring device.
Figure 2:
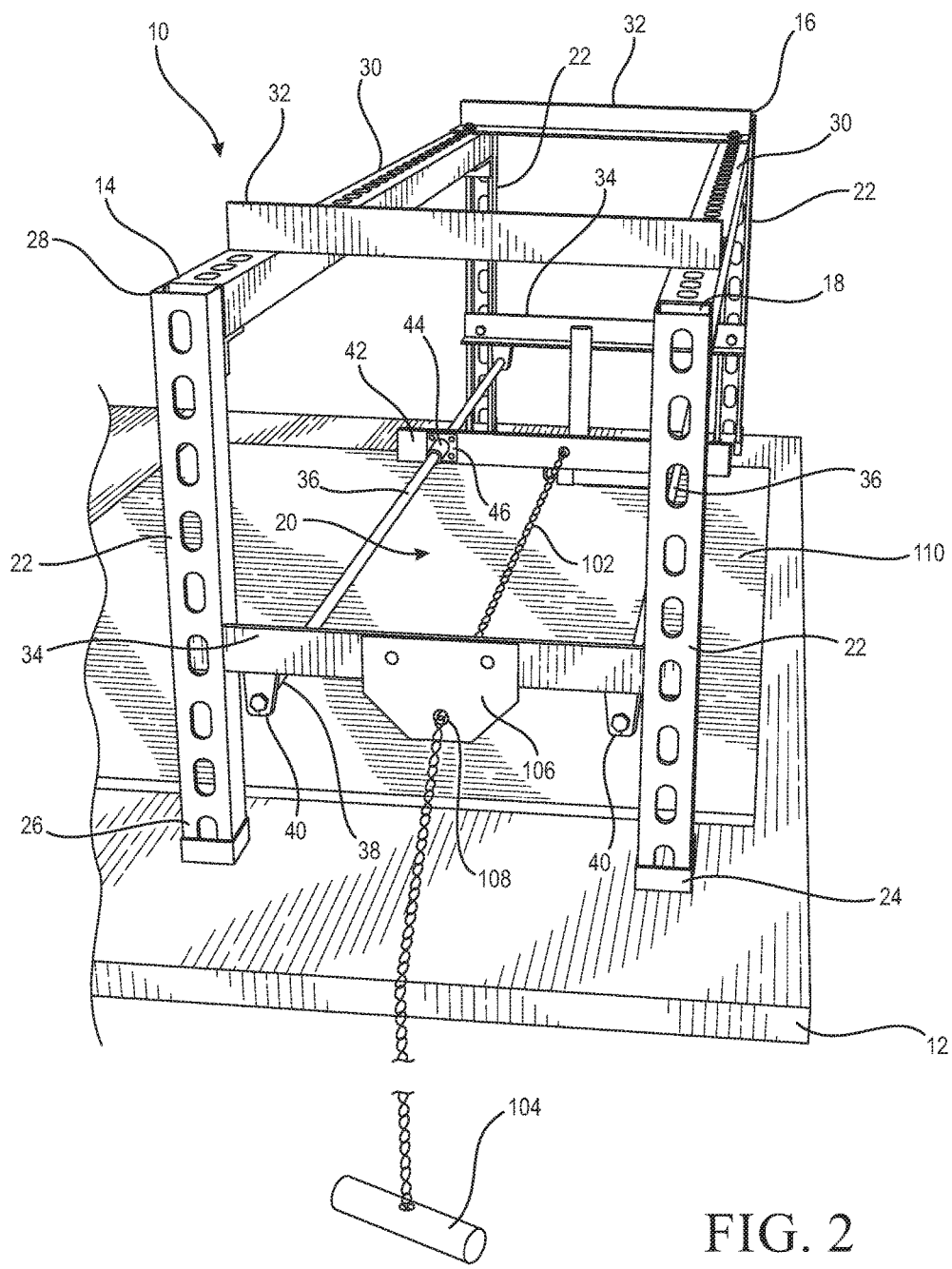
FIG. 2 is a rear end view of the device of FIG. 1.

Referring now to FIGS. 1 and 2, the present bench top board scoring device is generally designated 10 and is shown mounted on a substrate 12 such as a work table or the like. Included on the device 10 is a frame 14 having a first end 16 and an opposite second end 18, with a work area 20 defined between the first and second ends. Each of the first and second ends 16, 18 has at least one, and preferably a pair of legs 22 configured for contacting the substrate 12. In the preferred embodiment, each leg 22 is provided with a resilient, rubber-like foot 24 at a lower end 26. Opposite the lower end 26, each leg 22 has an upper end 28 which is connected to an elongate bar 30.

In the preferred embodiment, one of the elongate bars 30 is mounted between upper ends 28 of legs 22 at each of the first and second ends 16, 18. It is also preferred that the legs 22 and the elongate bars 30 are made of sturdy, lightweight material such as aluminum or the like. In the depicted embodiment, the aluminum bars are preferably perforated to reduce weight and cost. Also, at least one stabilizing bar 32 is mounted transversely to each of a pair of the elongate bars 30. For added structural support, a leg stabilizer 34 is connected to adjacent legs 22 at each of the two ends 16, 18. While other similar materials are contemplated, it is preferred that the stabilizer bar 32 and the leg stabilizer 34 are made of rigid, lightweight material such as aluminum, and formed as a conventional "L"-bracket stock. The frame components 22, 30, 32 and 34 are secured together to form a sturdy unit by brazing, welding, fasteners or the like as is known in the art.

A track 36 is connected to the frame 14, preferably between opposing leg stabilizers 34, and extends between the first end 16 and the second end 18. While other configurations are contemplated, it is preferred that the track 36 is made of a pair of generally cylindrical, parallel, solid rods, each extending between legs 22 at each of the opposing ends 16, 18, and mounted at or near a corresponding end 38 to a corresponding rod bracket 40 that depends from the leg stabilizer 34. The rod ends 38 are held in place in the bracket 40 by set screws, keys, a snap friction fit, chemical adhesive, welding or the like as is well known in the art.

A carriage 42 is slidably mounted to the track 36 for travel between the first and second ends 16, 18. While in the preferred embodiment, the carriage 42 is largely made of a length of aluminum "L"-bracket, other lightweight, rigid materials are contemplated. A pair of tube-like, low-friction, linear bearings 44 are each mounted using a flange 46 near a corresponding end of the carriage 42 preferably project towards the second end 18, and are aligned with and slidably engage the rods of the track 36 to slidably reciprocate relative to the fixed track along a straight line. The orientation of the linear bearings 44 may vary to suit the application. Also, while the size of the linear bearings 44 may vary to suit the application, in the preferred embodiment they are 0.5-inch size.

Referring now to FIGS. 1, 3, 5 and 6, an arm 50 has an upper surface 52, a pivot end 54 pivotally connected to the carriage 42, and an opposite knife mount end 56. In the preferred embodiment, the arm 50 is mounted centrally on the carriage 42, however other positions are contemplated. The pivot end 54 is secured to an underside 58 (FIG. 6) of the carriage 42, preferably to a block 60 secured to the carriage 42 and having a laterally projecting stubshaft 62. A transverse bore 64 (shown hidden) in the pivot end 54 is designed to have a close tolerance with, and pivotally engages the stubshaft 62. A locking pin 66 engages a corresponding throughbore (not shown) in the stubshaft 62 for holding the arm 50 in place and creating a zero lash bearing, so that the arm pivots relative to the carriage 42 without any significant lateral play.

Figure 3:
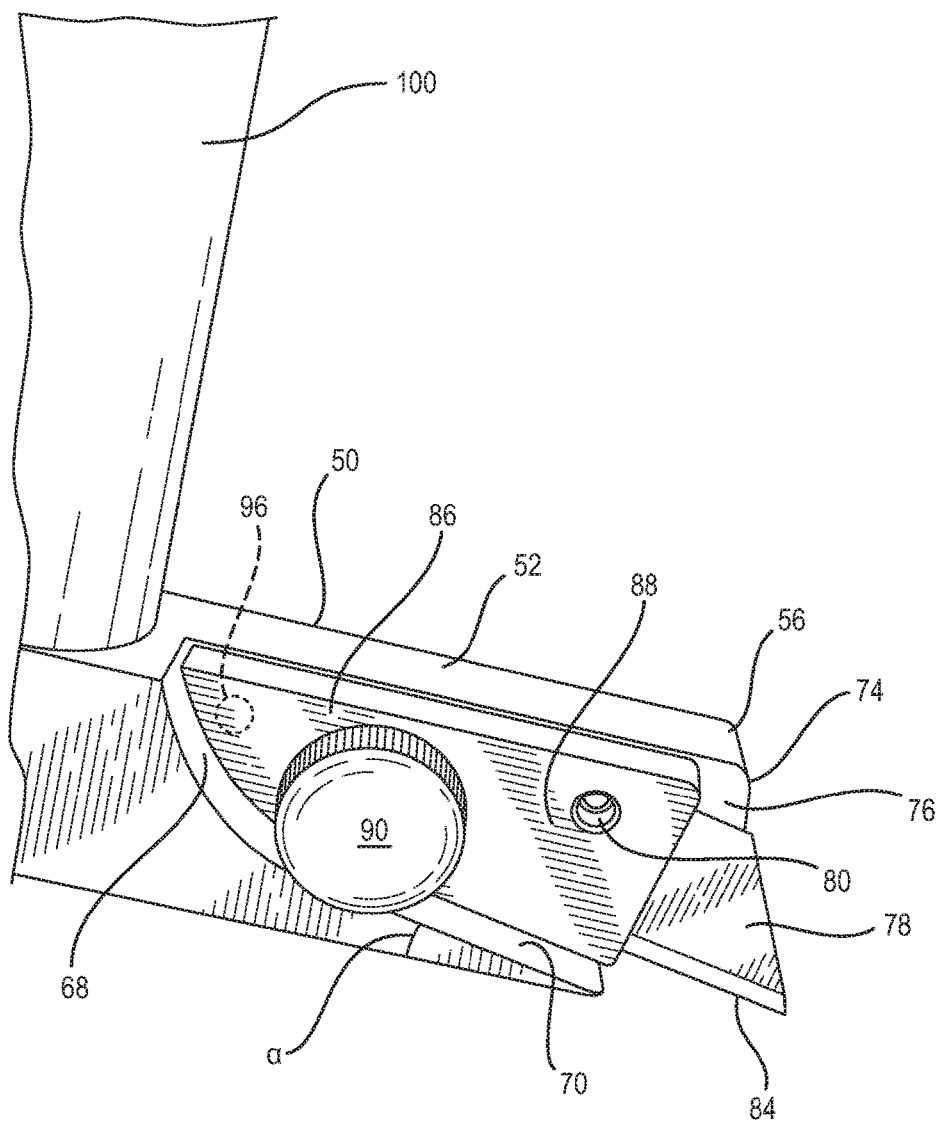
FIG. 3 is a fragmentary side perspective of the knife mount in the present board scoring device.
Figure 4:
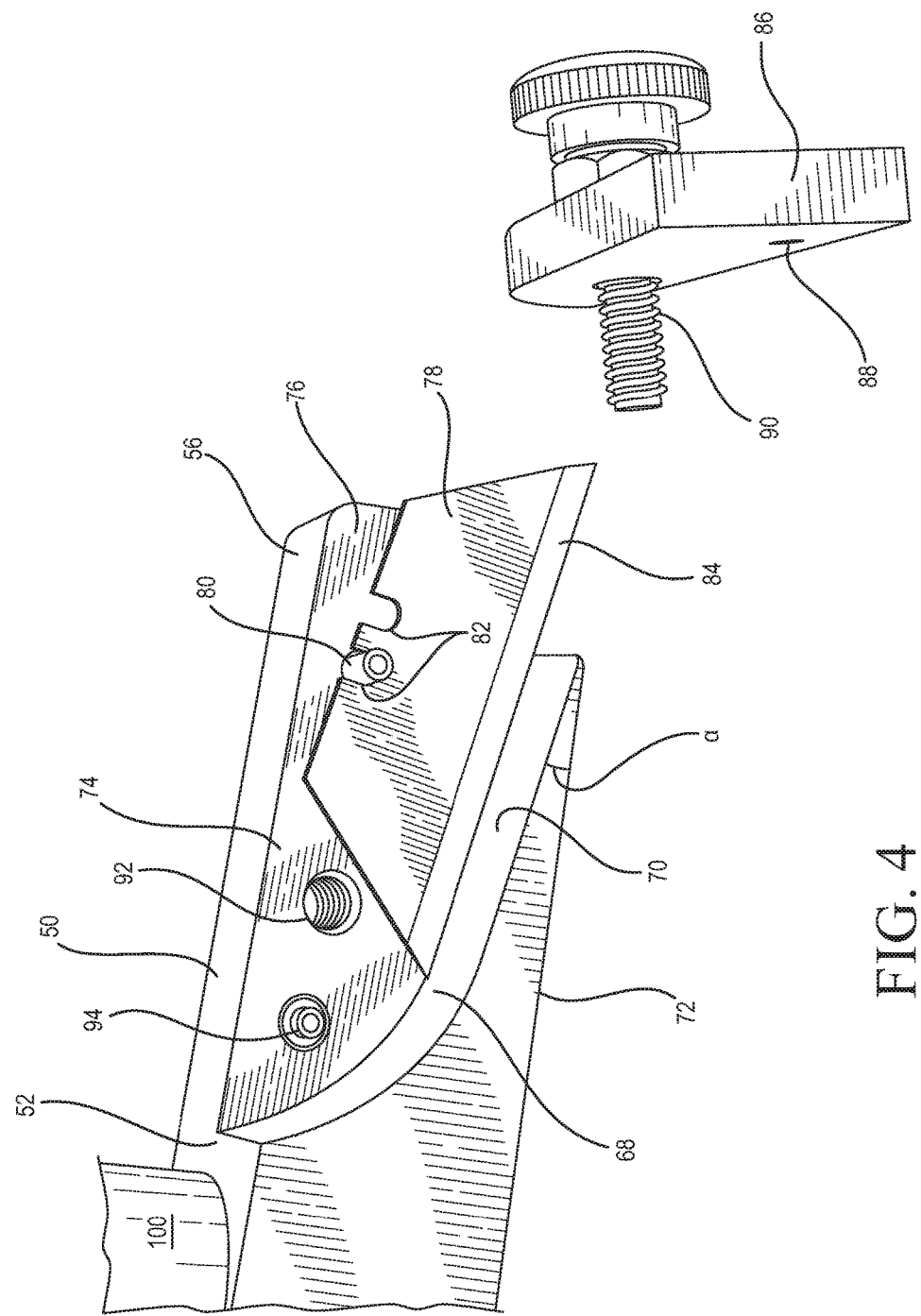
FIG. 4 is a fragmentary exploded perspective view of the knife mount of FIG. 3.

Referring now to FIGS. 3 and 4, the knife mount end 56 of the arm 50 includes a blade recess 68 having an angled floor or stage 70 defining an angle α relative to a lower arm surface 72, which is opposite the upper arm surface 52. In the preferred embodiment, α ranges from 10° to 30°, however wider ranges are contemplated. Also included on the knife mount end 56 is a generally vertical wall 74 having an inner face 76 against which a replaceable knife blade 78 is secured.

A transversely projecting pin 80 extends from the inner face 76 and provides a locating point for one of two notches 82 found in the knife blade 78, which is a conventional shop knife blade known to practitioners in the wallboard installation field. As is well known, the notches 82 are found on the blade 78 opposite a cutting edge 84, which when the blade is installed on the knife mount end 56, will rest on the floor 70 and will project from the arm end 56 at the angle α.

Once located on the pin 80, the knife blade 78 is further secured on the knife mount end 56 by a holding plate 86 having a locating opening 88 in registry with the pin 80, and having a threaded thumbscrew 90 engaging a threaded throughbore 92 in the vertical wall 74. It is contemplated that the knife mount end 56 is provided with a supplemental locating pin 94 engaging a complementary locating opening 96 (FIG. 3 shown hidden) in the holding plate 86. Once the holding plate 86 is located on the pins, 80, 94, the thumbscrew 90 is threadably secured to the vertical wall 74, securing the knife blade 78 in position. As seen in FIGS. 3 and 4, the removal and reinstallation of the knife blade 78 is accomplished without the use of tools.

Figure 5:
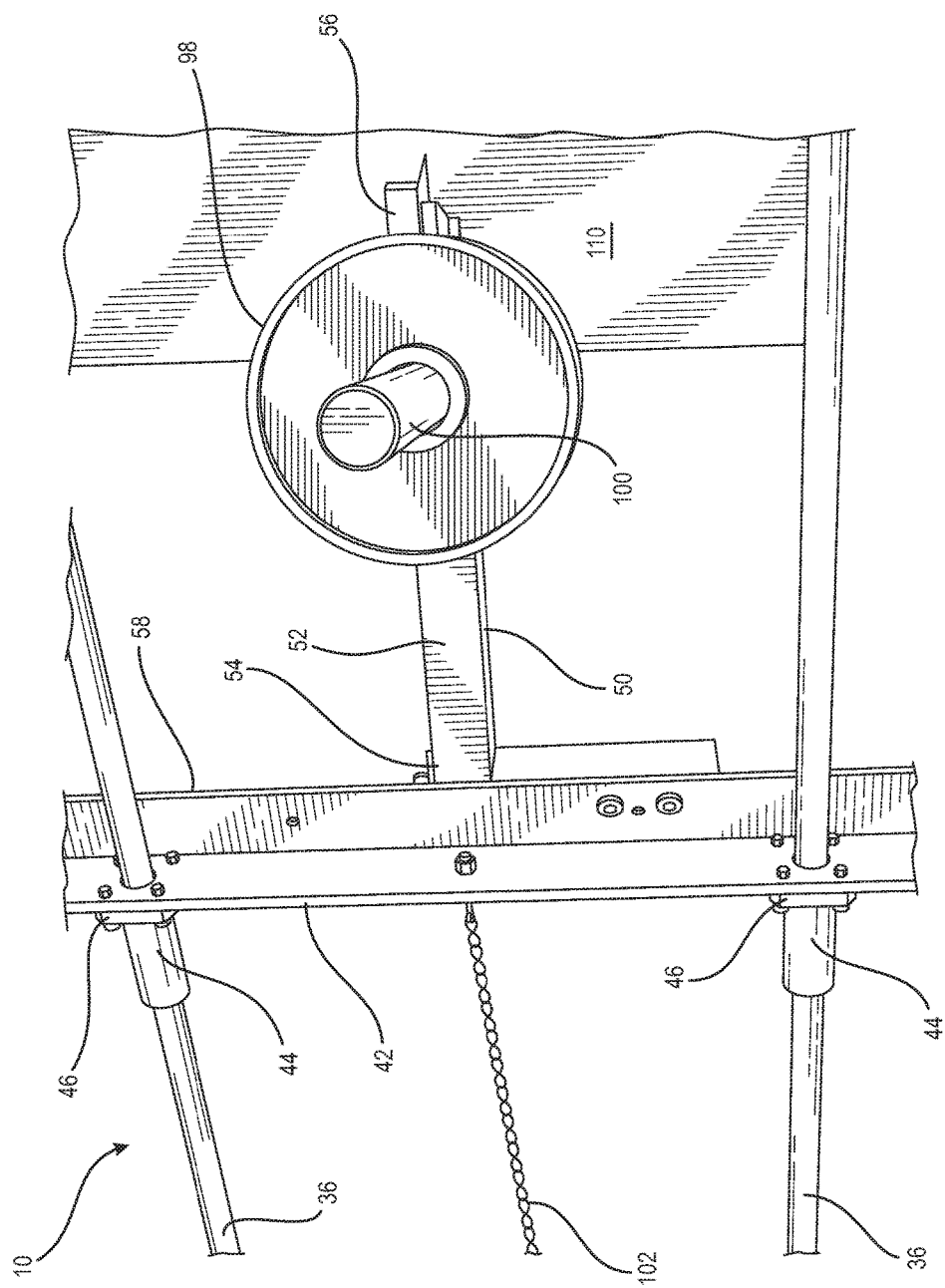
FIG. 5 is a fragmentary top view of the device of FIG. 1 showing the pivoting arm and carriage assembly.
Figure 6:
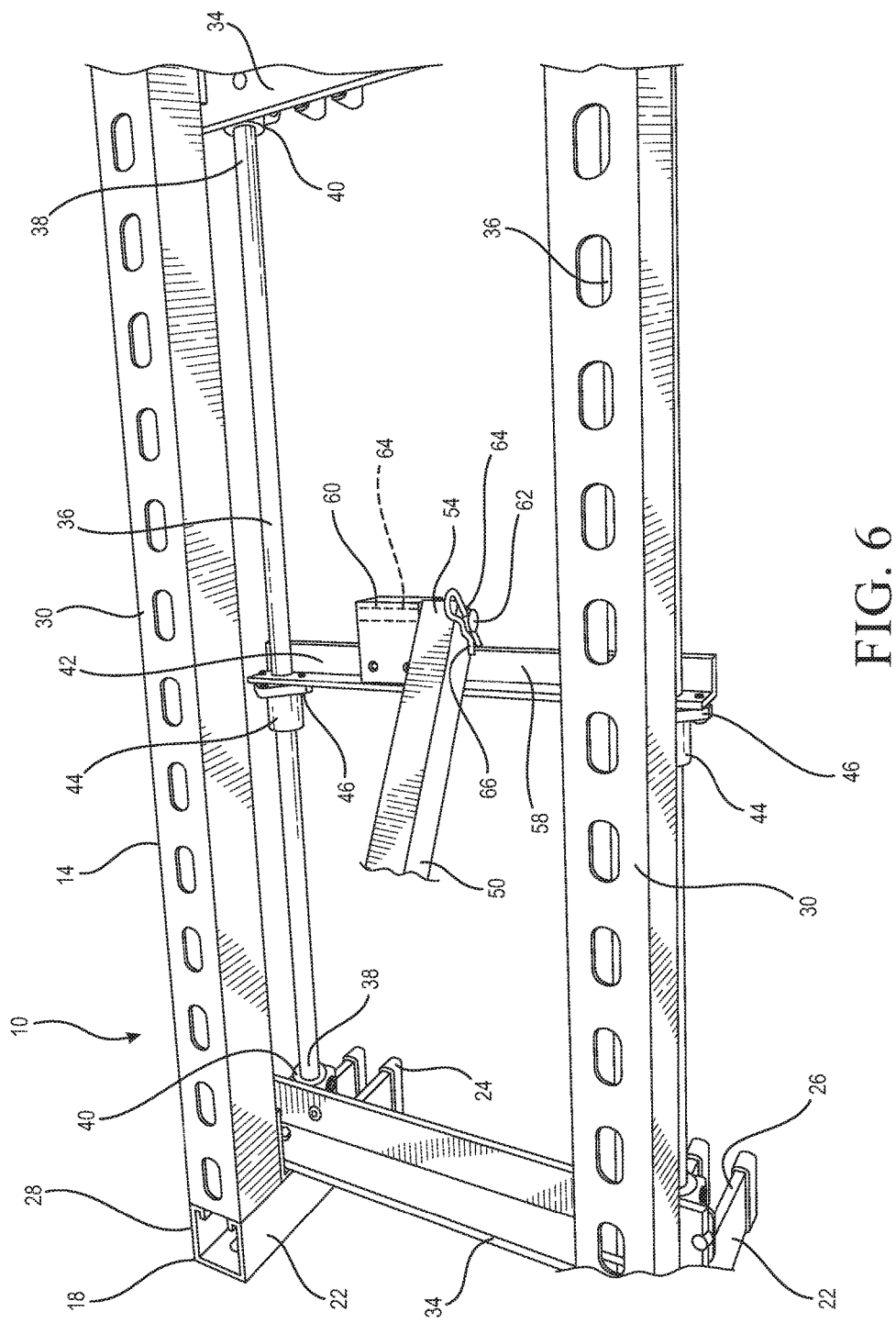
FIG. 6 is a fragmentary bottom view of the device of FIG. 5.

Referring now to FIGS. 1 and 5, another feature of the present bench top scoring device 10 is that a specific amount of weight is applied to the arm 50 to provide repeatable scoring performance. This weight or vertical force is applied by placing conventional barbell weight plates 98 (FIG. 5). The weights 98 are slidably mounted upon a weight post 100 associated with, and projecting from the arm 50. Since the weight plates 98 are produced in known increments, including 2.5, 5, 10 and 20 pounds, the amount of force applied to the arm 50 can be consistent for test purposes.

In the preferred embodiment, the weight post 100 has a diameter that is complementary to the conventional openings of conventional barbell weight plates, and projects generally vertically from the upper surface 52 of the arm 50. In an especially preferred embodiment, the weight post 100 projects normally from the upper surface 52 of the arm 50. Further, the weight post 100 is optionally located on the arm 50 closer to the knife mount end 56 than to the pivot end 54.

Referring now to FIGS. 2 and 5, a power transmission element 102 is connected to the carriage 42 for achieving user-generated movement of the carriage along the track 36. In the preferred embodiment, the power transmission element 102 is a metal chain with a user-engaging handle 104, however a rope, cable or other similar device is contemplated, as long as a user can remotely control the movement of the carriage 42 along the track 36. As seen in FIG. 2, the frame 14 is preferably provided with a support bracket 106 secured to one of the leg stabilizers 34 and having an opening 108 slidably accommodating the power transmission element 102.

In use, a wallboard panel 110 is placed on the substrate 12 in the work area 20. The carriage 42 is slid along the track 36 so that the knife blade 78 engages the panel 110 at an edge 112 as is customary in the field when scoring and popping of panels is performed. Suitable weights 98 are placed on the weight post 100, and the user then pulls the carriage 42 along the track using the power transmission element 102 until a score line is created along the full length of the sample panel 110. Next, the scored panel 110 is removed from the work area and is exposed to impact or popping force, either manually by a tester, or mechanically by a constant motion machine, described above, which applies a constant speed or load to panel samples until they fail, at which time a load reading is recorded. A suitable testing device is manufactured by Applied Test Systems of Butler, Pa., which measures the amount of force required to break the scored line. Such machines are well known in the wallboard manufacturing industry. After breaking or popping the panel 110, the popped edge can be examined for flatness and other characteristics.

While a particular embodiment of the present bench top board scoring device has been described herein, it will be appreciated by those skilled in the art that changes and modifications may be made thereto without departing from the invention in its broader aspects and as set forth in the following claims.

The invention claimed is:

1. A bench top board scoring device, comprising:
a frame having a first end and an opposite second end, a work area defined between said first and second ends, each end having at least one leg configured for contacting a substrate;
a track connected to said frame and extending between said first end and said second end;
a carriage slidably mounted to said track for travel between said first end and said second end;
an arm having an upper surface, a pivot end pivotally connected to said carriage, and an opposite knife mount end;
a knife blade mounted to said knife mount end;
a power transmission element connected to said carriage for achieving user-powered pulling movement of said carriage along said track, said arm pivoting along an axis transverse to a direction of said movement of said carriage along said track; and
a weight post associated with, and projecting from said arm, and constructed and arranged for receiving weights for exerting a force on said arm.

2. The bench top scoring device of claim 1, wherein said weight post projects generally vertically from said upper surface of said arm.

3. The bench top scoring device of claim 2, wherein said weight post projects normally from said upper surface of said arm.

4. The bench top scoring device of claim 1, wherein said weight post is located on said arm closer to said knife mount end than to said pivot end.

5. The bench top scoring device of claim 1, wherein said track is a pair of parallel rods, each rod extending between legs associated with said first and second ends.

6. The bench top scoring device of claim 5, wherein said carriage has a pair of generally cylindrical, linear bearings, each configured for slidably engaging an associated one of said rods.

7. The bench top scoring device of claim 1, wherein said knife blade is removably secured to said knife mount end of said arm using a user activated locking plate removable without tools.

8. The bench top scoring device of claim 1, further including a zero lash bearing on said carriage constructed and arranged for receiving said pivot end of said arm and retaining same to prevent lateral displacement while pivoting.

9. The bench top scoring device of claim 1, wherein said power transmission element is a pull chain and said frame includes a support bracket for said chain at at least one of said first and second ends.

10. A bench top board scoring device, comprising:
a frame having a first end and an opposite second end, a work area defined between said first and second ends, each end having at least one leg configured for contacting a substrate;
a track connected to said frame and extending between said first end and said second end;
a carriage slidably mounted to said track for travel between said first end and said second end;
an arm having an upper surface, a pivot end pivotally connected to said carriage, and an opposite knife mount end, said arm connected to said carriage only at said pivot end;
a knife blade mounted to said knife mount end;
a weight post associated with, and projecting from said arm, having a free end constructed and arranged for receiving weights for exerting a force on said arm; and
a power transmission element connected to said carriage for achieving user-powered pulling movement of said carriage along said track.

11. The bench top scoring device of claim 10, wherein said weight post projects generally normally from said upper surface of said arm.

12. The bench top scoring device of claim 10, wherein said weight post is located on said arm closer to said knife mount end than to said pivot end.

13. The bench top scoring device of claim 10, wherein said power transmission element is a pull chain and said frame includes a support bracket for said chain at at least one of said first and second ends.

14. The bench top scoring device of claim 10, wherein said track is a pair of parallel rods, each rod extending between legs associated with said first and second ends, and said carriage has a pair of generally cylindrical, linear bearings, each configured for slidably engaging an associated one of said rods.

15. The bench top scoring device of claim 10, further including a zero lash bearing on said carriage constructed and arranged for receiving said pivot end of said arm and retaining same to prevent lateral displacement while pivoting.

16. A bench top board scoring device, comprising:
a frame having a first end and an opposite second end, a work area defined between said first and second ends, each end having at least one leg configured for contacting a substrate;
a track connected to said frame and extending between said first end and said second end, said track is a pair of parallel rods, each rod extending between legs associated with said first and second ends;
a carriage slidably mounted to said track for travel between said first end and said second end, said carriage has a pair of generally cylindrical, linear bearings, each configured for slidably surrounding and engaging an associated one of said rods;
an arm having an upper surface, a pivot end pivotally connected to said carriage, and an opposite knife mount end;
a knife blade mounted to said knife mount end;
a power transmission element connected to said carriage for achieving user-powered pulling movement of said carriage along said track; and
a weight post associated with, and projecting from said arm, and constructed and arranged for receiving weights for exerting a force on said arm.

17. The bench top scoring device of claim 16, wherein said power transmission element is a pull chain and said frame includes a support bracket for said chain at at least one of said first and second ends.

\* \* \* \* \*